(12) United States Patent
Maity et al.

(10) Patent No.: US 8,711,340 B2
(45) Date of Patent: Apr. 29, 2014

(54) AUTO-ALIGNING SPECTROSCOPY SYSTEM (75) Inventors: Sandip Maity, Bangalore (IN); Chayan Mitra, Bangalore (IN); Rachit Sharma, Bangalore (IN)

(73) Assignee: General Electric Company, Niskayuna, NY (US)

( * ) Notice: Subject to any disclaimer, the term of this patent is extended or adjusted under 35 U.S.C. 154(b) by 296 days.

(21) Appl. No.: 13/118,631

(22) Filed: May 31, 2011

(65) Prior Publication Data

US 2012/0307241 A1 Dec. 6, 2012

(51) Int. Cl.
*G01N 21/00* (2006.01)
*G01B 11/14* (2006.01)

(52) U.S. Cl.
USPC .......................................... 356/72; 356/614

(58) Field of Classification Search
USPC .................. 356/300–301, 72–73, 402–425, 356/432–434, 614–624
See application file for complete search history.

(56) References Cited

U.S. PATENT DOCUMENTS

| | | | |
|---|---|---|---|
| 4,830,498 A * | 5/1989 | Nishimoto et al. | ........... 356/400 |
| 5,638,396 A | 6/1997 | Klimek | |
| 7,469,092 B2 | 12/2008 | Sappey et al. | |
| 2002/0027648 A1 * | 3/2002 | Van Der Laan et al. | ......... 355/71 |
| 2004/0213515 A1 * | 10/2004 | Pezeshki et al. | ................. 385/31 |
| 2008/0013887 A1 | 1/2008 | Sappey et al. | |
| 2010/0030347 A1 * | 2/2010 | Shindo | ............................ 700/59 |
| 2010/0140512 A1 * | 6/2010 | Suganuma et al. | ........ 250/504 R |
| 2012/0062871 A1 * | 3/2012 | Bugge | .............................. 356/51 |

OTHER PUBLICATIONS

Search Report and Written Opinion from corresponding EP Application No. 12168967.3-2217 dated Aug. 30, 2012.

* cited by examiner

*Primary Examiner* — Gregory J Toatley
*Assistant Examiner* — Hina F Ayub
(74) *Attorney, Agent, or Firm* — Seema S. Katragadda (57) ABSTRACT

An auto-aligning system is presented. One embodiment of the auto-aligning system includes a launcher unit configured to direct a first laser beam and a second laser beam through a chamber, wherein the first laser beam is co-linear with the second laser beam. The auto-aligning spectroscopy system further includes a receiver unit configured to receive the first laser beam and the second laser beam passing through the chamber. The receiver unit includes a first detector configured to determine an intensity of the first laser beam. The receiver unit also includes a second detector configured to determine a deviation of the second laser beam from a determined position. Further, the auto-aligning spectroscopy system includes a motorized stage configured to align the launcher unit to a base-line position based on the determined deviation of the second laser beam.

16 Claims, 4 Drawing Sheets

AUTO-ALIGNING SPECTROSCOPY SYSTEM

BACKGROUND

The disclosure relates generally to a spectroscopy system and more specifically to an automatically aligning spectroscopy system adapted for use in vibration prone environments, such as heat recovery steam generator (HRSG) chambers.

Many power requirements benefit from power generation plants that provide low cost energy with minimum environmental impact. In addition, the power generation plants provide better reliability and off-grid operation with alternate fuels such as biogas or landfill gas, with examples being gas turbines and combustion engines. The gas turbines are giant engines, which convert energy of hot pressurized combustion gases into mechanical energy by rotation of a turbine in the engines. Subsequently, this rotation of the turbine is utilized to generate electricity by using a generator. Thereafter, in a combined cycle plant, the exhaust or residual gases from the gas turbines are let out into the atmosphere through the HRSG chamber and a stack. These exhaust gases include traces of environment unfriendly gases that can be potentially hazardous to the atmosphere and human health. Therefore, it is of great interest and concern to identify the constituents and concentration of the exhaust gases and minimize the emission of unfriendly gases to the environment.

Currently, extractive techniques are available for monitoring the constituents and concentration of the exhaust gases, especially a target gas in the exhaust gases. The main idea of these techniques is that a sample of the exhaust gases is extracted and conveyed to analyzers through sample lines. Further, the constituents and concentration of the target gas is measured by offline measurement techniques, such as infrared and/or ultraviolet absorption measurements. Unfortunately there is a significant delay between the time of gas extraction and the analysis that follows to measure the constituents and concentration of the target gas. Thus, these techniques fail to facilitate a better control on emission of exhaust gases to the environment.

The alternative technique that can be employed to address this problem is Tunable Diode Laser Absorption Spectroscopy (TDLAS). TDLAS is typically implemented with diode lasers operating in the near-infrared and mid-infrared spectral regions. Various techniques of TDLAS for sensing and control of combustion processes have been developed. Commonly known techniques are wavelength modulation spectroscopy, frequency modulation spectroscopy, and direct absorption spectroscopy. Each of these techniques is based upon a determined relationship between the quantity and nature of laser beam received by a detector after the laser beam passes through an absorption media, such as gases inside the HRSG chamber. The laser beam, in specific spectral bands, may be absorbed by gas species in the chamber. The absorption spectrum of the laser beam received by the detector is used to determine the constituents and/or concentration of the gas species.

In these techniques, TDLAS is typically mounted in the stack to determine the constituents and/or concentration of the exhaust gases inside the chamber. The stack may be a small cylindrical pipe disposed at an outlet side of the HRSG chamber for releasing the residual gases to the atmosphere. However, the TDLAS may also be implemented in the HRSG chamber for desirable applications such as gas concentration measurement, gas temperature measurement, gas pressure measurement etc. Unfortunately, implementing the TDLAS in the HRSG chamber is difficult due to harsh conditions, vibrations, and thermal variations in the HRSG chamber. These conditions may cause misalignments of the TDLAS system leading to erroneous measurements of the exhaust gases.

Currently, there are various techniques to rectify the misalignment of TDLAS system. One way of correcting the misalignment of TDLAS system is to manually rectify or adjust the misalignment of the TDLAS system. However, manually adjusting the TDLAS system is a time consuming process as an operator may have to reach for the TDLAS system to manually adjust the TDLAS system. Also, manually adjusting the TDLAS system may be impractical in an operational power plant. Further, since the operator is unaware of a direction of misalignment of the TDLAS system, the operator may have to employ a trial and error method, which is again an inefficient and time consuming process.

It is therefore desirable to develop a design of a TDLAS system that reduces such erroneous measurements. Particularly, it is desirable to develop the design of the system that detects the misalignment in the TDLAS system and automatically aligns the TDLAS system, irrespective of the environmental conditions in and around the HRSG chamber.

BRIEF DESCRIPTION

Briefly in accordance with one aspect of the present technique, an auto-aligning spectroscopy system is presented. The auto-aligning spectroscopy system includes a launcher unit configured to direct a first laser beam and a second laser beam through a chamber, wherein the first laser beam is co-linear with the second laser beam. The auto-aligning spectroscopy system further includes a receiver unit configured to receive the first laser beam and the second laser beam passing through the chamber. The receiver unit includes a first detector configured to determine an intensity of the first laser beam. The receiver unit also includes a second detector configured to determine a deviation of the second laser beam from a determined position. Further, the auto-aligning spectroscopy system includes a motorized stage configured to align the launcher unit to a base-line position based on the determined deviation of the second laser beam.

In accordance with a further aspect of the present technique, a method of auto-aligning a spectroscopy system is presented. The method includes directing at least a first laser beam and a second laser beam from a launcher unit through a first window of a chamber, wherein the first laser beam is co-linear with the second laser beam. The method further includes receiving the co-linear first laser beam and the second laser beam at a second window of the chamber. The method also includes separating the second laser beam from the first laser beam such that the first laser beam is incident on a first detector and the second laser beam is incident on a second detector. Additionally, the method includes determining a deviation of the second laser beam incident on the second detector from a determined position. Further, the method includes aligning the launcher unit to a base-line position based on the determined deviation of the second laser beam.

In accordance with another aspect of the present technique, an auto-aligning spectroscopy system is presented. The auto-aligning spectroscopy system includes a launcher unit disposed adjacent to a first window of a chamber and configured to direct a first laser beam and a second laser beam through the chamber. The launcher unit includes a first laser source configured to emit the first laser beam, and a second laser source configured to emit the second laser beam. The launcher unit further includes a first dichroic mirror disposed at a first determined angle and configured to transmit the first laser beam through the first dichroic mirror and reflect the second laser beam along a direction of the first laser beam such that the second laser beam is co-linear with the first laser beam. The launcher unit also includes a first lens disposed downstream of the first dichroic mirror to collimate the first laser beam with the second laser beam. Further, the auto-aligning spectroscopy system includes a receiver unit disposed adjacent to a second window of the chamber and configured to receive the first laser beam and the second laser beam passing through the chamber. The receiver unit includes a second lens disposed adjacent to the second window of the chamber and configured to converge the first laser beam and the second laser beam. The receiver unit further includes a second dichroic mirror disposed adjacent to the second lens and configured to separate the first laser beam from the second laser beam. The receiver unit also includes a first detector disposed downstream of the second dichroic mirror and configured to determine an intensity associated with the first laser beam incident on the first detector. Furthermore, the receiver unit includes a second detector disposed downstream of the second dichroic mirror and configured to determine a deviation of the second laser beam from a determined position based on the second laser beam incident on the second detector. Additionally, the auto-aligning spectroscopy system includes a motorized stage configured to align the spectroscopy system to a base-line position based on the determined deviation of the second laser beam.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

As will be described in detail hereinafter, various embodiments of exemplary Tunable Diode Laser Absorption Spectroscopy (TDLAS) system and methods for automatically aligning the TDLAS system are presented. By employing the methods and TDLAS system described hereinafter, errors in measurement of exhaust gases can be substantially minimized.

Figure 1:
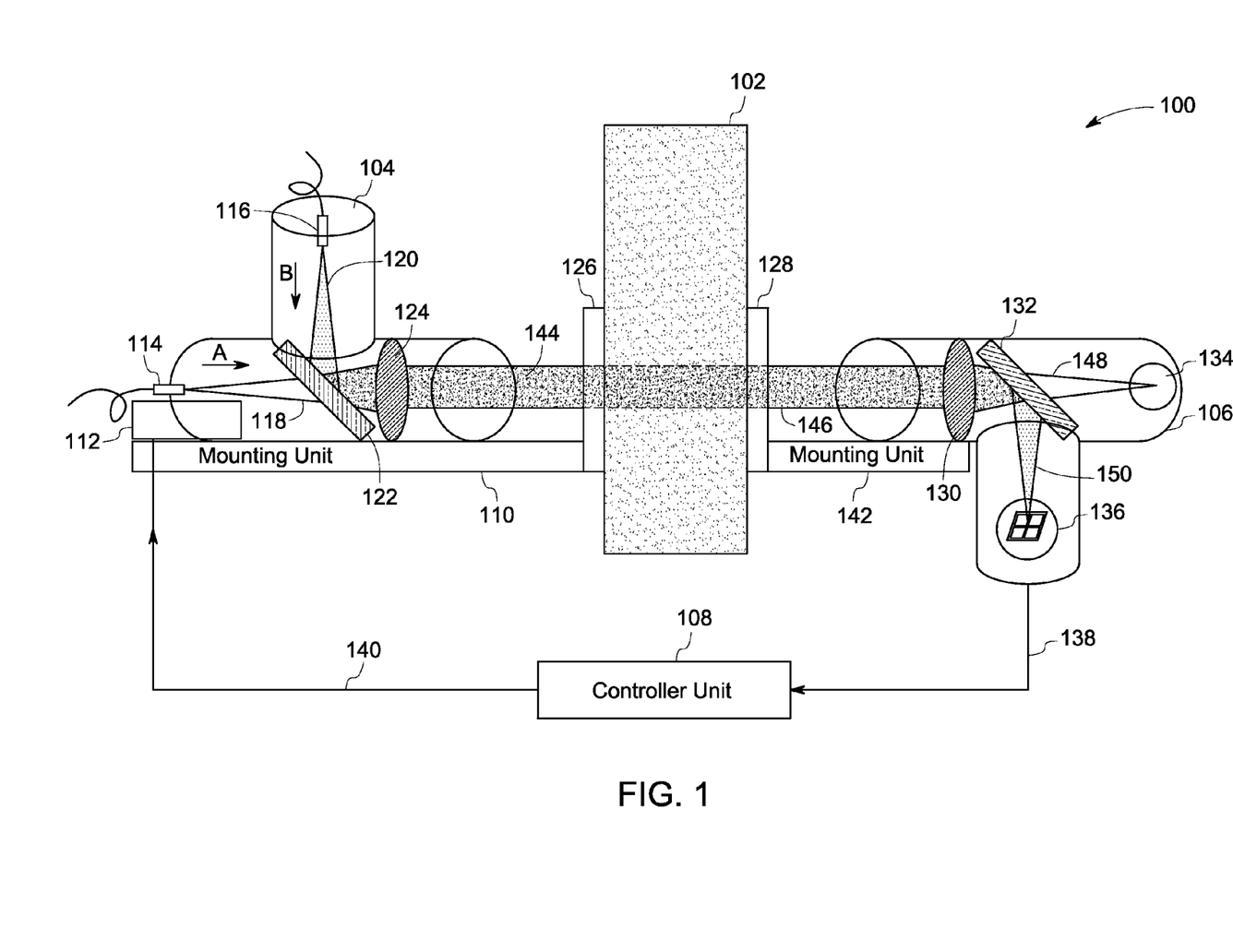
FIG. 1 is a diagrammatical illustration of a Tunable Diode Laser Absorption Spectroscopy (TDLAS) system, in accordance with aspects of the present technique.

Turning now to the drawings, and referring to FIG. 1, a diagrammatical illustration of an exemplary spectroscopy system 100, in accordance with aspects of the present technique, is depicted. It may be noted that in certain embodiments the spectroscopy system 100 may be a Tunable Diode Laser Absorption Spectroscopy (TDLAS) system. The spectroscopy system 100 is generally employed to determine the concentration and/or constituents of gas species in harsh vibration prone environments, such as a chamber 102. Typically, while determining or measuring the concentration and/or constituents of the gas species in the chamber 102, harsh environmental conditions, such as thermal vibrations inside the chamber 102 may result in the misalignment of the spectroscopy system 100 from a base-line position. The term base-line position is used to refer to a position of the spectroscopy system, where the concentration and/or constituents of gas species in the chamber 102 are measured with negligible or no error. This misalignment of spectroscopy system 100 may disadvantageously result in an erroneous measurement of the gas species in the chamber 102. Thus, it is highly desirable to maintain the spectroscopy system at the base-line position so as to minimize the errors in measurement of the gas species in the chamber 102. Also, it is desirable to automatically align the spectroscopy system 100 to the base-line position.

Further, in one example, the chamber 102 may be a Heat Recovery Steam Generator (HRSG) chamber that is coupled to a gas emission system such as a gas turbine or a combustion engine. In one embodiment, the chamber 102 may be referred to as an exhaust path for the gas emission systems. Particularly, the chamber 102 receives the exhaust or residual gases from the gas emission system, and emits such exhaust gases to the environment.

In addition, the gas species in the exhaust gases are classified into two main categories: major species and minor species. The major species include environment friendly gases such as $CO_2$, $H_2O$, $N_2$, and $O_2$. On the other hand, the minor species include environment unfriendly gases such as NOx, SOx, and CO. The minor species are undesirable gases as they can be potentially hazardous to the atmosphere and the environment. It is desirable to automatically align the spectroscopy system 100 to the base-line position to facilitate accurate measurement of these undesirable species.

In a presently contemplated configuration, the spectroscopy system 100 is illustrated diagrammatically as including a launcher unit 104, a receiver unit 106, and a controller unit 108. The launcher unit 104 is disposed on a first side of the chamber 102, while the receiver unit 106 is disposed on a second side of the chamber 102 that is opposite to the first side of the chamber 102. Particularly, the receiver unit 106 is positioned in a line-of-sight position with the launcher unit 104 to collect laser beams transmitted by the launcher unit 104 through the chamber 102.

In the embodiment illustrated in FIG. 1, the launcher unit 104 is mounted on a mounting unit 110 that is operatively coupled to a first window 126 of the chamber 102. The first window 126 may be an optical window that allows the laser beams to pass through the chamber 102 and blocks the exhaust gases from flowing out of the chamber 102. In one embodiment, the first window 126 may have a mounting flange (not shown in FIG. 1) to which one end of the mounting unit 110 is coupled. The other end of the mounting unit 110 supports the launcher unit 104.

In accordance with exemplary aspects of the present technique, the launcher unit 104 includes a first laser source 114, a second laser source 116, a first dichroic mirror 122, and a collimator 124. In one embodiment, the first laser source 114 is disposed adjacent to the first dichroic mirror 122. Also, the first laser source 114 is configured to generate and transmit a first laser beam 118 at a first determined wavelength toward the first dichroic mirror 122. The first determined wavelength is selected such that the characteristics of the first laser beam 118 are sensitive to absorption and/or scattering by the gas species in the chamber 102. Particularly, the first determined wavelength of the first laser beam 118 is selected such that any absorption and/or scattering of the first laser beam 118 by a target gas in the chamber 102 affects the intensity of the first laser beam 118. The term target gas may be used to refer to a gas whose concentration and/or constituents are to be determined to aid in the control of emission of such a gas to the environment. For example, the target gas may be nitrogen dioxide.

In the illustrated embodiment of FIG. 1, the first laser beam 118 is transmitted at near infrared wavelength toward the first dichroic minor 122. In one example, the first laser beam 118 is transmitted at a wavelength in a range from about 1350 nm to about 1750 nm. In another example, the first laser beam 118 is transmitted at a wavelength in a range from about 700 nm to about 2000 nm. The first laser beam 118 is optically transmitted in a determined direction 'A' as depicted in FIG. 1.

It may be noted that the launcher unit 104 is aligned to the base-line position. During operation, the alignment of spectroscopy system 100 and consequently the alignment of the launcher unit 104 may be disturbed from the base-line position.

In accordance with exemplary aspects of the present technique, the second laser source 116 is employed to determine any misalignment of the launcher unit 104 and/or physical disturbances in the chamber 102. In one example, the physical disturbances may be clogging and/or blockage of the first window 126 and/or a second window 128. The second laser source 116 is disposed in a determined spatial relationship with the first dichroic mirror 122. In one embodiment, the second laser source 116 is positioned substantially perpendicular to the first laser source 114. The second laser source 116 is configured to generate and transmit a second laser beam 120 at a second determined wavelength towards the first dichroic minor 122. The second determined wavelength is selected to be in a range such that the characteristics of the second laser beam 120 are insensitive to all the gas species in the chamber 102. Since the second laser beam 120 is insensitive to all the gas species in the chamber 102, any deviation of the second laser beam 120 at the receiver unit 106 may be interpreted as a misalignment of the launcher unit 104 and/or physical disturbances in the chamber 102. Thus, in accordance with exemplary aspects of the present technique, employing an additional laser beam, such as the second laser beam 120, along with the first laser beam 118 aids in the identification and subsequent rectification of any misalignment in the spectroscopy system 100.

In the illustrated embodiment of FIG. 1, the second laser beam 120 is transmitted at a wavelength in a range from about 400 nm to about 700 nm towards the first dichroic mirror 122. The second laser beam 120 is optically transmitted in a determined direction 'B' as depicted in FIG. 1.

Further, in one embodiment, the first dichroic mirror 122 is positioned at a first determined angle with respect to the first laser source 114 and the second laser source 116. Also, in certain embodiments, the first dichroic mirror 122 may be disposed inside a mounting cube (not shown in FIG. 1). The mounting cube is employed for initial adjustment of the first dichroic mirror 122 to the first determined angle. The first determined angle may be any angle that directs the second laser beam 120 to be co-linear with the first laser beam 118. Since the second laser beam 120 is co-linear with the first laser beam 118, any deviation of the first laser beam 118 may cause a corresponding deviation of the second laser beam 120. For example, if the first laser beam 118 deviates from an initial position, the second laser beam 120 also deviates from its initial or determined position. In the illustrated embodiment of FIG. 1, the first dichroic mirror 122 is positioned at an angle of about 45 degrees. However, use of other angles is also envisaged.

Moreover, the first dichroic mirror 122 receives the first laser beam 118 along the first direction 'A'. Concurrently, the first dichroic mirror 122 also receives the second laser beam 120 along the second direction 'B'. Upon receiving the first and second laser beams 118, 120, the first dichroic mirror 122 directs the first laser beam 118 through the first dichroic minor 122. However, the first dichroic minor 122 reflects the second laser beam 120 along a path of the first laser beam 118 such that the reflected second laser beam 120 is co-linear with the first laser beam 118. In one embodiment, the first dichroic minor 122 may be referred to as a beam combiner that combines the first laser beam 118 with the second laser beam 120 such that the second laser beam 120 is co-linear with the first laser beam 118.

In addition, the first laser beam 118 and the second laser beam 120 are collimated upstream of the chamber 102 by the collimator 124 that is disposed adjacent to the first dichroic minor 122. In one embodiment, the collimator 124 may be a first lens that is disposed downstream of the first dichroic minor to collimate the first laser beam 118 with the second laser beam 120. The co-linear first and second laser beams may generally be referenced by reference numeral 144. Thereafter, the co-linear first and second laser beams 144 are optically directed through the chamber 102 via the first window 126 of the chamber 102.

In the embodiment illustrated in FIG. 1, the receiver unit 106 is disposed in a reverse optical arrangement as that of the launcher unit 104. Reference numeral 146 generally refers to the co-linear first and second laser beams that pass through the chamber 102 and exit the chamber 102 through the second window 128. The receiver unit 106 is configured to collect the co-linear first and second laser beams 146 that pass through the chamber 102. It may be noted that the co-linear first and second laser beams 146 received by the receiver unit 106 may be partially disturbed and/or scattered while passing through the chamber 102.

The receiver unit 106 is also mounted on a mounting unit 142 that is operatively coupled to the second window 128 of the chamber 102. The second window 128 may be an optical window that allows the co-linear first and second laser beams 146 to exit the chamber 102 and blocks the exhaust gases from flowing out of the chamber 102. In one embodiment, the second window 128 may have a mounting flange (not shown in FIG. 1) to which one end of the mounting unit 142 is coupled. The other end of the mounting unit 142 supports the receiver unit 106.

Furthermore, in one embodiment, the receiver unit 106 includes a second lens 130, a second dichroic mirror 132, a first detector 134, and a second detector 136. The second lens 130 is disposed adjacent to the second window 128 and configured to converge the co-linear first and second laser beams 146 on to the second dichroic mirror 132 that is disposed adjacent to the second lens 130.

In a presently contemplated configuration, the second dichroic minor 132 is positioned at a second determined angle with respect to the first and second detectors 134 and 136. Here again, in one embodiment, the second dichroic minor 132 may be disposed inside a mounting cube (not shown in FIG. 1). The mounting cube is employed to make an initial adjustment to the second dichroic minor 132 so as to align the second dichroic minor 132 to the second determined angle. The second determined angle may be any angle that separates the components of the co-linear first and second laser beams 146 into a first laser beam and a second laser beam. In the embodiment illustrated in FIG. 1, the second dichroic minor 132 is positioned at an angle of about 45 degrees. The first laser beam received by the receiver unit 106 is generally represented by reference numeral 148, while the second laser beam received at the receiver unit 106 is generally represented by reference numeral 150.

Additionally, the second dichroic mirror 132 is configured to allow the first laser beam 148 to pass through such that the first laser beam 148 is incident on the first detector 134. Concurrently, the second dichroic mirror 132 reflects the second laser beam 150 such that the second laser beam 150 is incident on the second detector 136. Thus, the second dichroic mirror 132 separates the second laser beam 150 from the first laser beam 148.

Moreover, the first detector 134 is disposed downstream of the second dichroic mirror 132 to determine an intensity associated with the first laser beam 148. Particularly, the first detector 134 determines the concentration and/or constituents of the exhaust gases based on the intensity and other characteristics of the first laser beam 148. It may be noted that the target gas in the chamber 102 absorbs at least a portion of the first laser beam 148, which in turn reduces the intensity of the first laser beam 148. This reduction in intensity of the first laser beam 148 is used to identify the target gas in the chamber 102. In one embodiment, the first detector 134 may be an infrared (IR) photodiode that is used to measure the intensity of the first laser beam 148. Further, in one embodiment, the IR photodiode communicates the signals of the first laser beam 148 to an external unit, such as a laser absorption spectrometry (LAS) IR setup for measuring and analyzing the constituents and/or concentration of one or more target gases.

In accordance with aspects of the present technique, the second detector 136 is disposed downstream of the second dichroic minor 132 and is configured to determine a deviation of the second laser beam 150 from a determined position. In one embodiment, the determined position of the second laser beam 150 may be representative of a position of the second laser beam 150 that is incident on the center of the second detector 136. During initial testing of the spectroscopy system 100, the second detector 136 is adjusted by a kinematic mount or by adjusting screws of the mounting unit 142 such that the second laser beam 150 is incident on the center of the second detector 136, while the first laser beam 148 is incident on the center of the first detector 134. Particularly, the first detector 134 and the second detector 136 are initially adjusted such that the first laser beam 148 is incident on the center of the first detector 134, while the second laser beam 150 is incident on the center of the second detector 136.

As will be appreciated, during the operation of the spectroscopy system 100 or the power plant, there may be a misalignment of the spectroscopy system 100 due to harsh environmental conditions. This misalignment may consequently result in a deviation of the launcher unit 104 from the base-line position. For example, the thermal vibrations of the power plant may cause the launcher unit 104 to deviate from the base-line position. This misalignment or deviation of the launcher unit 104 results in deviation of the points of incidence of the first laser beam 148 and the second laser beam 150 on their respective detectors. Thus, the misalignment of the launcher unit 104 may disadvantageously result in erroneous measurement and/or analysis of the species in the target gas.

In accordance with exemplary aspects of the present technique, the second laser beam 150 is employed to aid in the detection and subsequent correction of any misalignment of the spectroscopy system 100. Particularly, the misalignment of the launcher unit 104 causes the second laser beam 150 to be incident at a first position on the second detector 136. The first position may be any position that is different from the determined position. Since the second laser beam 150 is insensitive to the gas species in the chamber 102, the change in position of the second laser beam 150 from the determined position to the first position may be attributed to the misalignment of the spectroscopy system 100. In one embodiment, this misalignment of the spectroscopy system 100 may be due to vibrations during startup, heating of the launcher unit 104, or thermal vibrations inside the chamber 102.

Additionally, in one embodiment, the second detector 136 may be a position sensitive photodetector that is specially employed to aid in detecting any misalignment of the spectroscopy system 100 and in automatically aligning the spectroscopy system 100 to the base-line position. In accordance with exemplary aspects of the present technique, the position sensitive photodetector may include a quadrant photodiode. The quadrant photodiode 136 aids in determining the position of incidence of the second laser beam 150. Particularly, the quadrant photodiode 136 generates three signals that are indicative of the deviation of the second laser beam 150 and are generally represented by reference numeral 138. Two of the signals indicate an X-Y position of the second laser beam 150 that is incident on the quadrant photodiode 136, while the other signal is indicative of a total power of the second laser beam 150. In one example, the X-Y position may be the first position of the second laser beam 150. These signals 138 are employed in the automatic aligning of the spectroscopy system 100. To that end, the signals 138 obtained from the quadrant photodiode 136 are communicated to the controller unit 108. The functioning of the second detector 136 will be described in greater detail with reference to FIG. 2.

In a presently contemplated configuration, the controller unit 108 is configured to align the launcher unit 104 back to the base-line position based on the deviation of the second laser beam 150. Particularly, the controller unit 108 receives the signals 138 from the second detector 136. The signals 138 are indicative of the deviation of the second laser beam 150 from the determined position. Further, the controller unit 108 generates an error signal 140 based on the received signals 138. The error signal 140 is then communicated to a motorized stage 112 to align the launcher unit 104 back to the base-line position. In one embodiment, the controller unit 108 may include a set of pre-stored instructions or code that computes the error signal 140 based on the received signals 138. In addition, the controller unit 108 automatically communicates the error signal 140 or command signal to the motorized stage 112 for automatically aligning the launcher unit 104 back to the base-line position. In one embodiment, the controller unit 108 may be disposed proximate to the chamber 102. In another embodiment, the controller unit 108 may be a host computer that is disposed at a remote location and wirelessly coupled to the launcher unit 104 and the receiver unit 106.

As previously noted, the motorized stage 112 is configured to align the launcher unit 104 back to the base-line position based on the error signal 140 received from the controller unit 108. Particularly, in one embodiment, the motorized stage 112 is mounted on the mounting unit 110 and is coupled to the launcher unit 104. The motorized stage 112 orients the launcher unit 104 in a direction corresponding to the error signal 140 so as to align the launcher unit 104 to the base-line position. By way of example, if the launcher unit 104 is displaced in the +X-direction, based on the error signal 140 the motorized stage 112 orients the launcher unit 104 in the −X-direction such that the launcher unit 104 is re-aligned to the base-line position.

Further, in one embodiment, the motorized stage 112 includes a two-axis actuator that is configured to orient the launcher unit 104 in at least two different directions and at least one angle to align the launcher unit 104 to the base-line position. The two-axis actuator in the motorized stage 112 orients the launcher unit 104 based on the error signal 140 received from the controller unit 108. Thus, by employing the second laser source 116, the second detector 136, and the controller unit 108, the misalignment of the spectroscopy system 100, and particularly the misalignment of the launcher unit 104 is easily identified and the launcher unit 104 is automatically aligned back to the base-line position. In addition, automatically aligning the launcher unit 104 to the base-line position allows the receiver unit 106 to perform an error free measurement of the exhaust gases in the chamber 102. In some embodiments, the motorized stage aligns the spectroscopy system 100 to the base-line position. For example, the motorized stage 112 may be disposed at the receiver unit 106 to align the launcher unit 104 and/or the receiver unit 106 to the base-line position.

Figure 2:
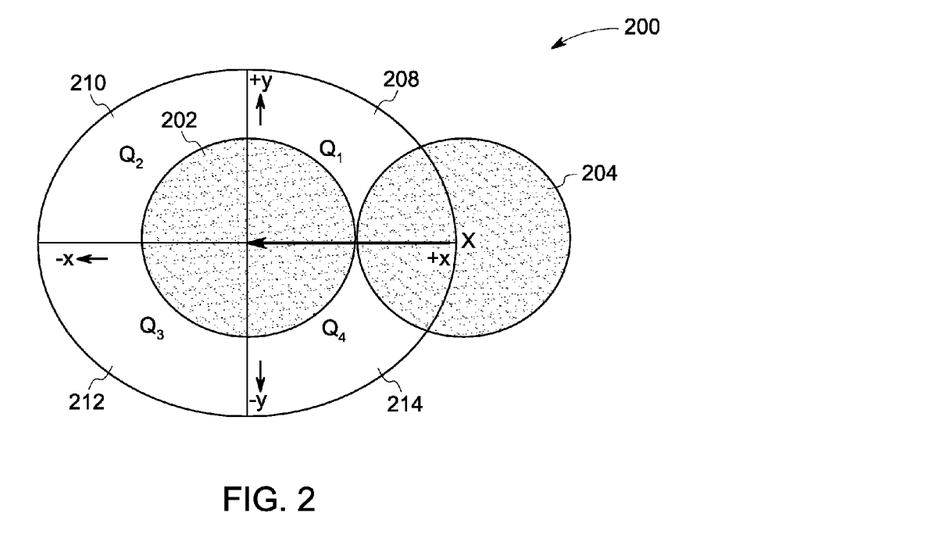
FIG. 2 is a diagrammatical illustration of a detector for use in the TDLAS system, in accordance with aspects of the present technique.

FIG. 2 is a diagrammatical illustration of one embodiment 200 of the second detector 136 in the spectroscopy system 100 of FIG. 1, in accordance with aspects of the present technique. For ease of understanding of the present technique, the components of FIG. 2 are described with reference to the components of FIG. 1. The second detector 200 may be a photosensitive detector that is disposed in the receiver unit 106 to determine any misalignment of the spectroscopy system 100, especially misalignment of the launcher unit 104. As previously noted, the misalignment of the launcher unit 104 may be due to harsh environmental conditions in the chamber 102 or around the launcher unit 104. By way of example, the harsh environmental conditions may include vibrations during startup, heating of the launcher unit 104, or thermal vibrations inside the chamber 102.

In accordance with exemplary aspects of the present technique, the second detector 200 includes a quadrant photodiode. This quadrant photodiode 200 is employed for determining any misalignment of the spectroscopy system 100. Particularly, the quadrant photodiode 200 determines any deviation of the second laser beam 150 from a determined position 202. As previously noted, the determined position 202 may be representative of a position where the second laser beam 150 is incident on the quadrant photodiode 200 with no power loss or acceptable power loss in the second laser beam 150. In one embodiment, the determined position may be on the center (0, 0) of the quadrant photodiode 200.

To that end, during initial testing of the spectroscopy system 100, the quadrant photodiode 200 is adjusted manually and/or by using electrical signals so that the second laser beam 150 is incident on the center of the quadrant photodiode 200. Accordingly, this position of the second laser beam 150 on the quadrant photodiode 200 is referred to as the determined position 202. Further, during the operation of the spectroscopy system 100, the spectroscopy system 100 may be misaligned due to certain environmental conditions. This misalignment of spectroscopy system 100 may consequently result in the misalignment of the launcher unit 104, which in turn may result in the deviation of the first laser beam 118 and the second laser beam 120 generated by the launcher unit 104. In addition, the deviation of the laser beams 118, 120 generated by the launcher unit 104 may result in a deviation of the laser beams 148, 150 that exit the chamber 102.

However, since the first laser beam 148 is sensitive to gas species in the chamber 102, the deviation of the first laser beam 148 may also be due to scattering and/or absorption of the gas species in the chamber 102. Therefore, it may be difficult to identify the misalignment by employing only the first laser beam 148 as the deviation of the first laser beam 148 may be due to misalignment and/or due to scattering and/or absorption of the gas species in the chamber 102. Thus, according to aspects of the present technique, in order to overcome such ambiguity, the second laser beam 150 that is insensitive to all the gas species in the chamber 102 is employed along with the first laser beam 148 for identifying any misalignment in the spectroscopy system 100, especially the misalignment of launcher unit 104.

Further, any misalignment in the spectroscopy system 100 causes the second laser beam 150 to deviate from the determined position 202. By way of example, the misalignment of the spectroscopy system 100 may result in the second laser beam 150 now being incident on a first position 204 on the quadrant photodiode 200. The first position 204 may be any position that is different from the determined position 202.

In a presently contemplated configuration, the quadrant photodiode 200 is employed to generate at least two signals, for example an X signal and a Y signal that indicate the position of the second laser beam 150 (see FIG. 1). Moreover, in one embodiment, the quadrant photodiode 200 includes a common substrate that acts as a cathode (not shown in FIG. 2). Also, the quadrant photodiode 200 may include two or four photodiode elements. In the embodiment depicted in FIG. 2, the quadrant photodiode 200 includes four separate photodiode elements 208, 210, 212, 214 that are positioned on the common substrate. The four photodiode elements 208, 210, 212, 214 are separated by a small gap on the common substrate. Particularly, each of the four photodiode elements 208, 210, 212, 214 on the common substrate forms one of the four quadrants Q1, Q2, Q3, Q4 as depicted in FIG. 2.

Additionally, each of the photodiode elements 208, 210, 212, 214 acts as an anode or an active area that illuminates when a light spot or a laser beam falls on the corresponding active area. For example, if the second laser beam 150 is incident on the quadrant Q1, the photodiode element 208 is illuminated. In another example, if the second laser beam 150 is incident on the quadrants Q1 and Q4, the corresponding photodiode elements 208 and 214 are illuminated.

Moreover, the anode or the active area of each photodiode element is individually identifiable so that the light spot or the second laser beam 150 illuminating a single quadrant can be electrically characterized as being associated with that quadrant. However, as depicted in FIG. 2, this second laser beam 150 is translated across two photodiode elements 208 and 214. Accordingly, energy associated with the second laser beam 150 is also distributed across the adjacent photodiode elements 208 and 214. Further, this distribution of energy over the two photodiode elements 208 and 214 generates a corresponding electrical signal from each of the photodiode elements 208 and 214. These electrical signals are utilized to determine the position of the second laser beam 150 on the quadrant photodiode 200.

In the illustrated embodiment of FIG. 2, the second laser beam 150 is incident on the first position 204 that is different from the determined position 202. As noted hereinabove, during the initial testing of the spectroscopy system 100, the quadrant photodiode 200 is adjusted so that the second laser beam 150 is incident on a center position 202 of the quadrant photodiode 200, where the center position is representative of the determined position 202. At the determined position 202, the quadrant photodiode 200 generates at least two position signals $X_1$ and $Y_1$. These two position signals $X_1$ and $Y_1$ are indicative of the second laser beam 150 being incident on the determined position 202, which in turn is indicative of the launcher unit 104 being aligned to the base-line position.

As previously noted, any misalignment of the spectroscopy system 100 results in the second laser beam 150 deviating from the determined position 202 and being incident at the first position 204 on the quadrant photodiode 200, for example. Since the first position 204 of the second laser beam is spread across the quadrants Q1 and Q4, the photodiode elements 208 and 214 corresponding to quadrants Q1 and Q4 are illuminated. Moreover, based on the energy associated with the second laser beam 150 that is incident on the quadrant photodiode 200, the photodiode elements 208 and 214 generate a corresponding electrical signal. In one embodiment, the photodiode element 208 generates an electrical signal $i_1$ and the photodiode element 214 generates a corresponding electrical signal $i_4$. Also, the electrical signals $i_1$ and $i_4$ are utilized to determine at least two position signals $X_2$ and $Y_2$. The position signal $X_2$ indicates a displacement of the second laser beam 150 along the X-axis in the four quadrants Q1, Q2, Q3, and Q4. In a similar fashion, the position signal $Y_2$ indicates a displacement of the second laser beam 150 along the Y-axis in the four quadrants Q1, Q2, Q3, and Q4, as depicted in FIG. 2. Thus, by employing the position signals $X_2$ and $Y_2$, the deviation of the second laser beam 150 from the determined position 202 may be determined. Additionally, the direction of the deviation of the second laser beam 150 is also determined based on values of the position signals $X_2$ and $Y_2$. For example, if the value of the $X_2$ signal is a negative value and the value of the $Y_2$ signal is a positive value, then it may be determined that the second laser beam 150 is deviating towards the quadrant $Q_2$ of FIG. 2.

In one embodiment, the position signals $X_2$ and $Y_2$ are determined by employing the following equations.

$$X_2 = \frac{-[(i_1 + i_2) - (i_3 + i_4)]}{[i_1 + i_2 + i_3 + i_4]} \quad (1)$$

$$Y_2 = \frac{-[(i_2 + i_3) - (i_1 + i_4)]}{[i_1 + i_2 + i_3 + i_4]} \quad (2)$$

In equations (1) and (2), $i_1$ represents the electrical signal received from the photodiode element 208 in the quadrant Q1, while $i_2$ represents an electrical signal received from the photodiode element 210 in the quadrant Q2. Similarly, $i_3$ represents the electrical signal received from the photodiode element 212 in the quadrant Q3, while $i_4$ represents an electrical signal received from the photodiode element 214 in the quadrant Q4. Since the first position 204 of the second laser beam 150 is spread only across the quadrants Q1 and Q4, the elements 210 and 212 are not illuminated. Hence, while electrical signals $i_1$ and $i_4$ corresponding to Q1 and Q4 are generated, no electrical signals corresponding to Q2 and Q3 are generated.

In addition, along with the position signals $X_2$ and $Y_2$, a total intensity of the second laser beam 150 is also determined. Particularly, in one embodiment, the total intensity of the second laser beam 150 is determined by summing the electrical signals $i_1$, $i_2$, $i_3$, $i_4$ received from a corresponding photodiode element in the quadrant photodiode 200. This total intensity of the second laser beam 150 is used to determine a total power $P_2$ of the second laser beam 150 at the receiver unit 106. In a similar manner, a total power $P_1$ of the second laser beam 120 is computed at the launcher unit 104 prior to passing the second laser beam 120 through the chamber 102. For example, $P_1$ represents the total power of the second laser beam 120 at the launcher unit 104.

Moreover, the total intensity of the second laser beam 150 or the power $P_2$ of the second laser beam 150 is used to determine scattering of the second laser beam 150. Since the second laser beam 150 is insensitive to the gas species in the chamber 102, the scattering of the second laser beam 150 may be mainly due to dust particles on at least one of the first window 126 and the second widow 128 of the chamber 102. Additionally, the scattering of the second laser beam 150 may be due to any physical disturbance to the windows 126, 128 or the chamber 102. This scattering of the second laser beam 150 leads to a loss in the total intensity of the second laser beam 150, which further reduces the power $P_2$ of the second laser beam 150. Thus, by comparing the power $P_2$ of the second laser beam 150 with the power $P_1$ of the second laser beam 120, clogging or blockage of the windows 126, 128 or any other physical disturbances in the chamber 102 are determined.

Alternatively, the scattering of the second laser beam 150 is detected by comparing the power $P_2$ of the second laser beam 150 with an initial power $P_{int}$ of the second laser beam 150. The initial power $P_{int}$ may be the total power that is obtained when the second laser beam 150 is incident on the determined position 202 on the quadrant photodiode 200. By comparing the power $P_2$ of the second laser beam 150 with an initial power $P_{int}$ of the second laser beam 150, power loss $P_L$ of the second laser beam 150 is determined as:

$$P_L = P_{int} - P_2 \quad (3)$$

The determined power loss $P_L$ is employed to determine any misalignment of the spectroscopy system 100. In particular, the determined power loss $P_L$ is used to determine if the power loss $P_L$ is due to scattering of the second laser beam 150 or due to the misalignment of the spectroscopy system 100 and more particularly, the misalignment of the launcher unit 104. If the power loss $P_L$ is less than or equal to a determined threshold value and the position signals $X_1$ and $Y_1$ indicate that there is no deviation of the second laser beam 150 from the determined position, then it may be determined that the loss in power is due to the scattering of the second laser beam 150. In one embodiment, the determined threshold value may be about 1% of the initial power $P_{int}$. As previously noted, the scattering of the second laser beam 150 may be mainly due to dust particles on the windows 126, 128 or in the chamber 102. This scattering of the second laser beam 150 may result in a minimal deviation of the second laser beam 150 from the determined position 202. Thus, the power loss $P_L$ due to scattering of the second laser beam 150 may also be minimal or negligible.

However, if the power loss $P_L$ is greater than the determined threshold value, then it may be determined that the loss in power is due to the misalignment of the launcher unit 104. Particularly, in the embodiment illustrated in FIG. 2, the second laser beam 150 is incident on the first position 204, where the first position 204 includes an edge or periphery of the quadrant photodiode 200. More specifically, while a portion of the second laser beam 150 is incident on the Q1 and Q4 quadrants of the quadrant photodiode 200, some portion of the second laser beam 150 is incident outside the boundary of the quadrant photodiode 200. Consequently, only a portion of the second laser beam 150 is detected by the photodiode elements 208, 214. Thus, the power $P_2$ of the second laser 150 beam is substantially less when compared to the initial power $P_{int}$. Specifically, in this example, the power loss $P_L$ of the second laser beam 150 may be more than the determined threshold value of about 1% of the initial power $P_{int}$. Accordingly, it is determined that the loss in power of the second laser beam 150 is due to the misalignment of the launcher unit 104. Thus, by using information related to the position and power of the second laser beam 150 at the receiver unit 106, it is possible to determine any misalignment of the spectroscopy system 100 and/or physical disturbances in the chamber 102.

Further, in one embodiment, the power loss $P_L$ of the second laser beam 150 due to the scattering of the second laser beam 150 may be used to determine an absorption power loss $P_{AB}$ of the first laser beam 148. Particularly, the first detector 134 determines a total power loss $P_{TTL}$ of the first laser beam 148 based on an intensity of the first laser beam 148. The total power loss $P_{TTL}$ includes at least the absorption power loss $P_{AB}$ and a scattering power loss $P_{SC}$ of the first laser beam 148. The scattering power loss $P_{SC}$ is due to scattering of the first laser beam 148 by dust particles in the chamber 102 and/or blockage of the first and second windows 126, 128 of the chamber 102. Similarly, the absorption power loss $P_{AB}$ is due to absorption of the first laser beam 148 by the gas species in the chamber 102. It may be noted that in an ideal spectroscopy system, the gas species are typically measured based only on the absorption loss $P_{AB}$ of the first laser beam 148. However, in a conventional spectroscopy system, the gas species are measured based on the total power loss $P_{TTL}$ that includes both the scattering power loss $P_{SC}$ and the absorption power loss $P_{AB}$ of the first laser beam 148. Unfortunately, separating the absorption power loss $P_{AB}$ from the scattering power loss $P_{SC}$ of the first laser beam 148 is a difficult process. Accordingly, such a measurement based on both the power losses $P_{AB}$, $P_{SC}$ results in an error as both the power losses $P_{AB}$, $P_{SC}$ are considered, rather than considering only the absorption power loss $P_{AB}$.

Thus, in accordance with exemplary aspects of the present technique, the absorption power loss $P_{AB}$ of the first laser beam 148 is determined by comparing the total power loss $P_{TTL}$ of the first laser beam 148 with the power loss $P_L$ of the second laser beam 150. Particularly, a percentage (%) power loss $P_L$ of the second laser beam 150 is employed to determine a percentage (%) power loss $P_{SC}$ of the first laser beam 148. Further, this percentage (%) power loss $P_{SC}$ of the first laser beam 148 is used to determine the absorption power loss $P_{AB}$ of the first laser beam 148. In one embodiment, the scattering power loss $P_{SC}$ of the first laser beam 148 may be determined by employing the following equation.

$$\frac{Q(\lambda_1)}{Q(\lambda_2)} = \frac{\%\text{ power loss at }\lambda_1}{\%\text{ power loss at }\lambda_2} \quad (4)$$

In equation (4), λ1 represents the wavelength of the first laser beam 148, while λ2 represents the wavelength of the second laser beam 150. Further, Q represents the scattering efficiency of the laser beams 148, 150. Since the values of wavelengths λ1 and λ2 are known and the percentage (%) power loss $P_L$ of the second laser beam 150 is computed, the percentage (%) power loss $P_{SC}$ of the first laser beam 148 may be calculated. Further, the percentage (%) power loss $P_{SC}$ of the first laser beam 148 so determined is used to compute the absorption power loss $P_{AB}$ of the first laser beam 148. The absorption power loss $P_{AB}$ may subsequently be used for scattering correction of the first laser beam 148. In addition, the absorption power loss $P_{AB}$ of the first laser beam 148 is used to accurately measure the constituents and concentration of the gas species. Thus, the scattering power loss $P_L$ of the second laser beam 150 is used for scattering correction of the first laser beam 148, thereby minimizing erroneous measurement of the gas species in the chamber 102.

Figure 3:
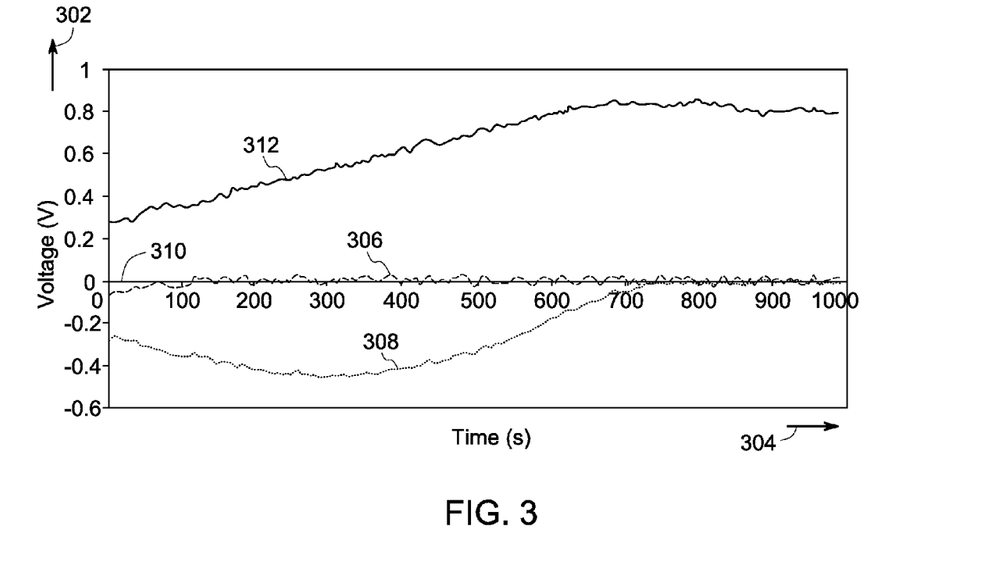
FIG. 3 is a graphical representation of position signals of a second laser beam incident on the detector of FIG. 2, in accordance with aspects of the present technique.

FIG. 3 is a graphical representation 300 of position signals of the second laser beam 150 (see FIG. 1) that are incident on the second detector 136 (see FIG. 1), in accordance with aspects of the present technique. For ease of understanding of the present technique, the graph 300 corresponds to the second laser beam 150 (see FIG. 1) that is incident at the first position 204 on the quadrant photo diode 200 of FIG. 2. In particular, in FIG. 3, values of position signals 306 and 308 are plotted as a variation of a voltage 302 over time 304. Also, a line 310 represents the position signals $X_1$ and $Y_1$ of FIG. 2, where the position signals $X_1$ and $Y_1$ are generated when the second laser beam 150 is incident on the center or the determined position 202 (see FIG. 2) of the quadrant photodiode 200 (see FIG. 2).

Further, the position signals 306 and 308 correspond to the first position 204 (see FIG. 2) of the second laser beam 150, as depicted in FIG. 2. Particularly, the position signal 308 corresponds to the position signal $X_2$. In a similar manner, the position signal 306 corresponds to the position signal $Y_2$. Moreover, in the example of FIG. 2, since the first position 204 of the second laser beam 150 is shifted only along the X-axis, there is a variation in the values of the position signal $X_2$ and is represented by the curve 308 in FIG. 3. However, since there is no deviation of the second laser beam 150 along the Y-axis in the example of FIG. 2, the value of position signal $Y_2$ remains substantially similar to the value of the position signal $Y_1$ as depicted by a curve 306 in FIG. 3. Thus, any deviation of the second laser beam 150 from the determined position 202 results in the generation of at least two position signals indicative of the deviation along with a direction of the deviation on the quadrant photodiode 200.

In addition, curve 312 represents the total power $P_2$ of the second laser beam 150 that is incident on the first position 204 of the quadrant photodiode 200 of FIG. 2. Since the second detector 136 detects only a portion of the second laser beam 150, the power loss $P_L$ of the second laser beam 150 is more than the determined threshold value of about 1% of the initial power $P_{int}$. Thus, the total power $P_2$ of the second laser beam 150 is represented as a varying voltage curve 312. It may be noted that if there is no power loss $P_L$ in the total power $P_2$ of the second laser beam 150, then the curve 312 may be represented as a horizontal line instead of a varying voltage curve.

Figure 4:
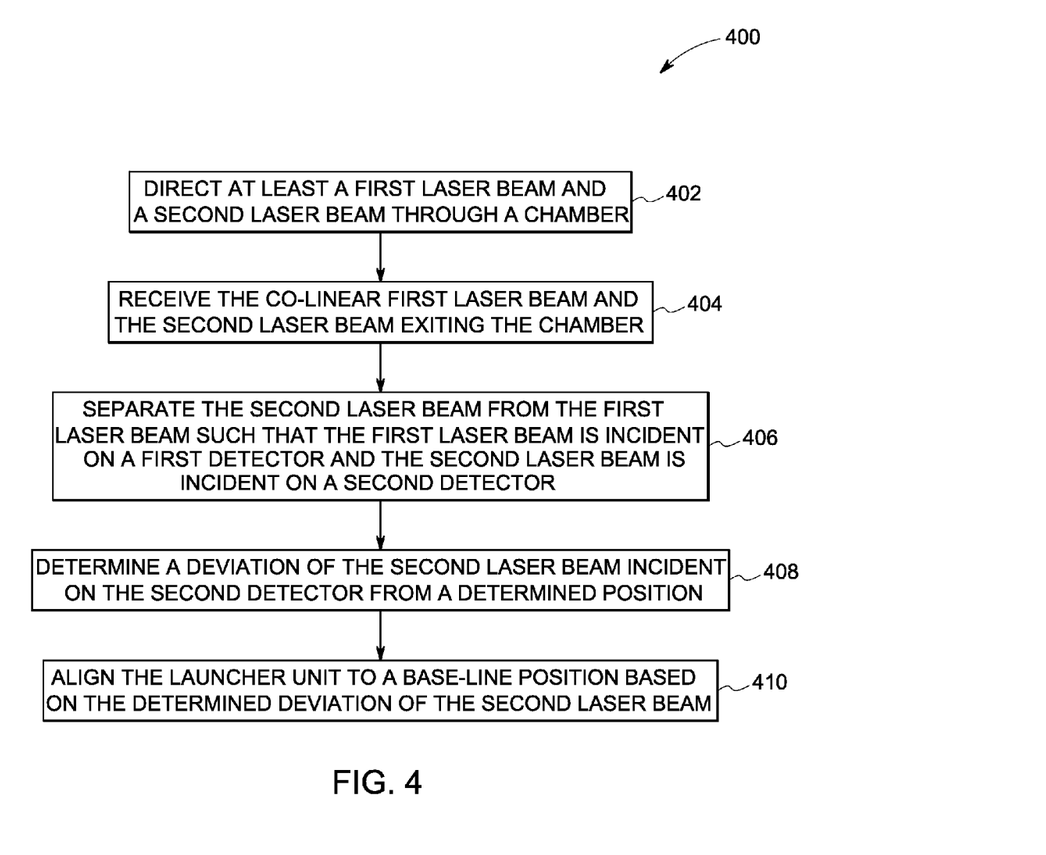
FIG. 4 is a flow chart illustrating a method for automatically aligning the TDLAS system, in accordance with aspects of the present technique.

Referring now to FIG. 4, a flow chart 400 illustrating a method for automatically aligning a spectroscopy system, such as the spectroscopy system 100 of FIG. 1, in accordance with aspects of the present technique, is depicted. Specifically, the method entails monitoring the alignment of the spectroscopy system 100 to detect any misalignment of the spectroscopy system 100 and automatically correcting the detected misalignment to align the spectroscopy system 100 back to a base-line position. For ease of understanding of the present technique, the method is described with reference to the components of FIGS. 1 and 2. The method begins at a step 402, where the first laser beam 118 and the second laser beam 120 are directed through the chamber 102 via the first window 126 of the spectroscopy system 100. Particularly, the launcher unit 104 having the beam combiner 122 receives the first laser beam 118 and the second laser beam 120 from a respective laser beam source 114, 116. Further, the beam combiner 122 combines the first laser beam 118 with the second laser beam 120 such that the second laser beam 120 is co-linear with the first laser beam 118. In one embodiment, the beam combiner 122 includes the first dichroic mirror 122 that allows or transmits the first laser beam 118 to pass through the first dichroic mirror 122, while reflecting the second laser beam 120 along a direction of the first laser beam 118 such that the second laser beam 120 is co-linear with the first laser beam 118, as depicted in FIG. 1. Thereafter, the combined beam 144 that includes the co-linear first laser beam 118 and the second laser beam 120 is directed through the chamber 102 via the first window 126.

Subsequently, at step 404, the receiver unit 106 receives the co-linear first and second laser beams 146 that exit the second window 128 of the chamber 102. The second window 128 is disposed opposite to the first window 126 of the chamber 102, in one embodiment.

Also, at step 406, the co-linear first and second laser beams 146 are separated such that the first laser beam 148 is incident on the first detector 134 and the second laser beam 150 is incident on the second detector 136. Particularly, the receiver unit 106 includes the beam splitter 132 that separates the second laser beam 150 from the first laser beam 148. In one embodiment, the beam splitter 132 includes the second dichroic mirror 132 that transmits the first laser beam 118 through the second dichroic mirror 132 such that the first laser beam 148 is incident on the first detector 134. Concurrently, the second dichroic mirror 132 also reflects the second laser beam 150 such that the second laser beam 150 is incident on the second detector 136, such as the quadrant photodiode 200 of FIG. 2.

Further, at step 408, the second detector 136 determines any deviation of the second laser beam 150 from the determined position 202 of FIG. 2. In one embodiment, the determined position 202 may be a position where the second laser beam 150 is incident on the center of the second detector 136. The deviation of the second laser beam 150 may be due to harsh environmental conditions, which cause the second laser beam 150 to deviate from the determined position 202 and instead be incident on the first position 204 on the second detector 136. The first position 204 may be any position that is different from the determined position 202. In one embodiment, the second detector 136 includes a quadrant photodiode 200 that generates at least two position signals X, Y based on the first position 204 of the second laser beam 150 on the quadrant photodiode 200. The position signal X indicates an X-coordinate of the first position 204 on the quadrant photodiode 200. In a similar manner, the position signal Y indicates a Y-coordinate of the first position 204 on the quadrant photodiode 200. These position signals X, Y are used to determine the deviation of the second laser beam 150 from the determined position 202. Additionally, the quadrant photodiode 200 generates a power signal that indicates a total intensity of the second laser beam 150. The power signal is used to determine whether the deviation of the second laser beam 150 is due to scattering of the second laser beam 150 or due to misalignment of the launcher unit 104.

The position signals X, Y and the power signal are subsequently communicated to the controller unit 108. The controller unit 108 may be either positioned proximate to the chamber 102 or placed at a remote location. The controller unit 108 generates an error signal 140 based on the received position signals X, Y and the power signal. The error signal 140 is also referred to as a command signal and is indicative of a deviation of the second laser beam 150 from the determined position 202. The error signal 140 is then communicated to the motorized stage 112 to align the launcher unit 104 back to a base-line position, as depicted by step 410. The motorized stage 112 that is coupled to the launcher unit 104 orients the launcher unit 104 along a direction corresponding to the error signal 140. This orientation of the launcher unit 104 realigns the launcher unit 104 to the base-line position. The aligning of the launcher unit 104 is explained in greater detail with reference to FIG. 5.

Figure 5:
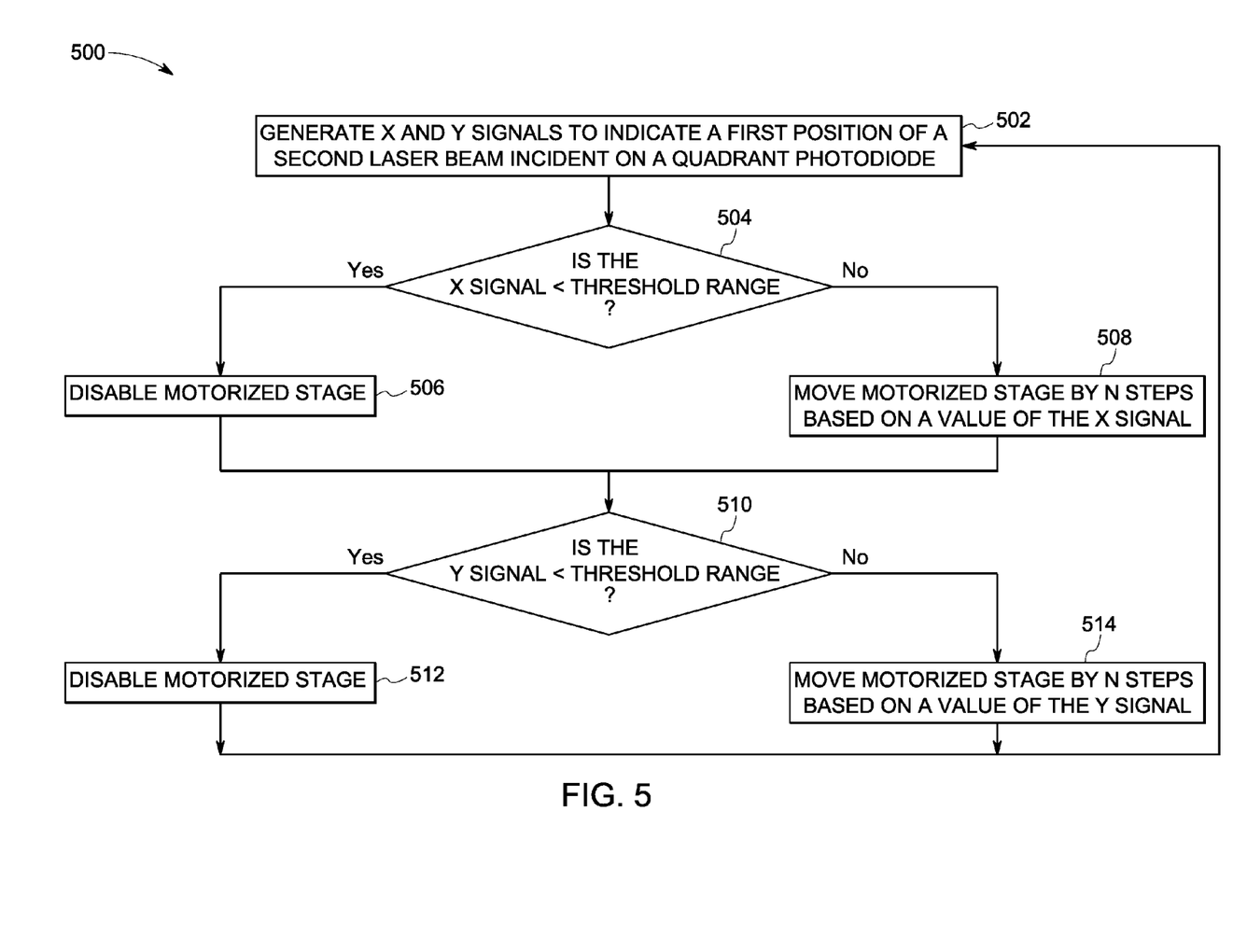
FIG. 5 is a flow chart illustrating a method for aligning a launcher unit of the TDLAS system, in accordance with aspects of the present technique.

FIG. 5 is a flow chart 500 illustrating a method for aligning the launcher unit 104 of a spectroscopy system such as the spectroscopy system 100 of FIG. 1, in accordance with aspects of the present technique. It may be noted that the steps 408 and 410 of FIG. 4 are explained in greater detail with reference to the flow chart 500 of FIG. 5. For ease of understanding of the present technique, the method is described with reference to the components of FIG. 1 and FIG. 2. The method begins at a step 502, where the second detector 136 (see FIG. 1), for example the quadrant photodiode 200 (see FIG. 2), generates position signals X and Y to indicate the first position 204 of the second laser beam 150 that is incident on the second detector 136. The position signal X indicates the deviation of the second laser beam 150 along the X-axis, while the position signal Y indicates the deviation of the second laser beam 150 along the Y-axis. The position signals X and Y are then communicated to the controller unit 108.

At step 504, the controller unit 108 verifies whether the position signal X is below a determined threshold range. The determined threshold range may be defined as a range outside which the deviation of the second laser beam 150 along the X-axis may be attributed to the misalignment of the spectroscopy system 100. Particularly, at step 504, if it is verified that the position signal X is below the determined threshold range, the motorized stage 112 that is employed to align the launcher unit 104 is disabled, as indicated by step 506.

On the other hand, at step 504, if it is determined that the position signal X is above the determined threshold range, the motorized stage 112 is moved by 'N' steps based on a value of the position signal X, as indicated by step 508. Particularly, the motorized stage 112 is translated by 'N' steps to realign the launcher unit 104 to the base-line position. In one example, the motorized stage 112 may include a step motor that is moved by about 10 steps based on the value of the position signal X. In one embodiment, the motorized stage 112 includes at least two actuators, an X-actuator and a Y-actuator. The X-actuator is employed to move the launcher unit 104 by 'N' steps in the X-direction. If desired a motorized stage may additionally or alternatively be situated at the receiver unit 106 to orient the receiver unit 106 so that the spectroscopy system 100 is aligned back to the base-line position.

Subsequent to steps 506 or 508, the controller unit 108 verifies a value of the position signal Y, as indicated by step 510. Specifically, at step 510, the controller unit 108 verifies whether the position signal Y is below a determined threshold range. The determined threshold range may be defined as a range outside which the deviation of the second laser beam 150 along the Y-axis may be attributed to the misalignment of the spectroscopy system 100. Particularly, at step 510, if it is verified that the position signal Y is below the determined threshold range, the motorized stage 112 that is employed to align the launcher unit 104 is disabled, as indicated by step 512.

With returning reference to step 510, if it is determined that the position signal Y is above the determined threshold range, the motorized stage 112 is moved by 'N' steps in the Y-direction based on a value of the position signal Y, as indicated by step 514. In one example, the step motor may be moved by about 10 steps corresponding to the value of the position signal Y. As previously noted, the motorized stage 112 includes the X-actuator and the Y-actuator. The Y-actuator is employed to move the launcher unit 104 by about 'N' steps in the Y-direction based on the value of the position signal Y. Subsequent to steps 512 or 514, steps 502 to 514 may be repeated for another set of position signals.

With returning reference to FIG. 4, consequent to the operation of steps 402-410 of FIG. 4, the launcher unit 104 is aligned to the base-line position by the motorized stage 112 based on the position signals X, Y received from the receiver unit 106, and the second detector 136 in particular.

The method and system described hereinabove aid in automatically aligning the TDLAS system to the base-line position, especially the launcher unit irrespective of the environmental conditions around the TDLAS system or in the chamber. Also, since the TDLAS system is automatically aligned, the erroneous measurement of exhaust gases in the chamber is significantly reduced. In addition, since the TDLAS system is implemented in the real time and the TDLAS system is also automatically aligned in the real-time, any delay in the measurement/analysis of the exhaust gases in the chamber may be substantially minimized While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An auto-aligning spectroscopy system, comprising:
a launcher unit configured to direct a first laser beam and a second laser beam through a chamber, wherein the first laser beam is co-linear with the second laser beam;
a receiver unit configured to receive the first laser beam and the second laser beam passing through the chamber, wherein the receiver unit comprises:
a first detector configured to determine an intensity of the first laser beam;
a second detector configured to:
generate at least two signals indicative of a first position of the second laser beam incident on the second detector, wherein the first position is different from a determined position;
generate at least one signal indicative of a power associated with the second laser beam;
determine a deviation of the second laser beam from the determined position;
a controller unit configured to:
determine a power loss of the second laser beam based on the power associated with the second laser beam;
compare the determined power loss of the second laser beam with a determined threshold value;
identify a scattering of the second laser beam when the power loss of the second laser beam is less than the determined threshold value and there is no deviation of the second laser beam from the determined position; and
a motorized stage configured to align the launcher unit to a base-line position when the power loss of the second laser beam is greater than the determined threshold value.

2. A method of auto-aligning a spectroscopy system, the method comprising:
directing at least a first laser beam and a second laser beam from a launcher unit through a first window of a chamber, wherein the first laser beam is co-linear with the second laser beam;
receiving the co-linear first laser beam and the second laser beam at a second window of the chamber;
separating the second laser beam from the first laser beam such that the first laser beam is incident on a first detector and the second laser beam is incident on a second detector;
generating at least two signals indicative of a first position of the second laser beam incident on the second detector, wherein the first position is different from a determined position;
generating at least one signal indicative of a power associated with the second laser beam;
determining a deviation of the second laser beam incident on the second detector from the determined position;
determining a power loss of the second laser beam based on a power associated with the second laser beam;
aligning the launcher unit to a base-line position when the determined power loss of the second laser beam is greater than a determined threshold value;
identifying a scattering of the second laser beam when the determined power loss is less than the determined threshold value;
determining an absorption power loss of the first laser beam based on the determined power loss of the second laser beam when the scattering of the second laser beam is identified; and
measuring a gas species in the chamber based on the determined absorption power loss of the first laser beam.

3. The method of claim 2, wherein aligning the launcher unit to the base-line position comprises:
generating an error signal by a controller unit based on the determined deviation of the second laser beam; and
driving a motorized stage coupled to the launcher unit based on the error signal to align the launcher unit to the base-line position.

4. The method of claim 2, wherein directing at least the first laser beam and the second laser beam comprises:
generating the first laser beam at a first wavelength, wherein the first laser beam is sensitive to one or more species in the chamber;
generating the second laser beam at a second wavelength, wherein the second laser beam is insensitive to the one or more species in the chamber;
combining the first laser beam with the second laser beam such that the second laser beam is co-linear with the first laser beam; and
collimating the first laser beam and the second laser beam upstream of the chamber.

5. An auto-aligning spectroscopy system, comprising:
a launcher unit disposed adjacent to a first window of a chamber and configured to direct a first laser beam and a second laser beam through the chamber, wherein the launcher unit comprises:
a first laser source configured to emit the first laser beam;
a second laser source configured to emit the second laser beam;
a first dichroic mirror disposed at a first determined angle and configured to:
transmit the first laser beam through the first dichroic mirror;
reflect the second laser beam along a direction of the first laser beam such that the second laser beam is co-linear with the first laser beam;
a first lens disposed downstream of the first dichroic mirror to collimate the first laser beam with the second laser beam;
a receiver unit disposed adjacent to a second window of the chamber and configured to receive the first laser beam and the second laser beam passing through the chamber, wherein the receiver unit comprises:
a second lens disposed adjacent to the second window of the chamber and configured to converge the first laser beam and the second laser beam;

a second dichroic mirror disposed adjacent to the second lens and configured to separate the first laser beam from the second laser beam;

a first detector disposed downstream of the second dichroic mirror and configured to determine an intensity associated with the first laser beam incident on the first detector;

a second detector disposed downstream of the second dichroic mirror and configured to:
determine a deviation of the second laser beam from a determined position based on the second laser beam incident on the second detector;

a motorized stage configured to align the spectroscopy system to a base-line position when a power loss of the second laser beam is greater than a determined threshold value; and a controller unit configured to identify a scattering of the second laser beam when the power loss of the second laser beam is less than the determined threshold value and there is no deviation of the second laser beam from the determined position.

6. The auto-aligning spectroscopy system of claim 5, wherein the controller unit is coupled to the motorized stage and the receiver unit and configured to:
generate an error signal based on the determined deviation of the second laser beam; and
drive the motorized stage based on the error signal to align the launcher unit to the base-line position.

7. The auto-aligning spectroscopy system of claim 6, wherein the motorized stage comprises a two-axis actuator to orient the launcher unit in one or more directions and at least one angle to align the launcher unit to the base-line position.

8. An auto-aligning spectroscopy system, comprising:
a launcher unit configured to direct a first laser beam and a second laser beam through a chamber, wherein the first laser beam is co-linear with the second laser beam;
a receiver unit configured to receive the first laser beam and the second laser beam passing through the chamber, wherein the receiver unit comprises:
a first detector configured to determine an intensity of the first laser beam;
a second detector configured to:
determine a deviation of the second laser beam from a determined position;
determine a power loss of the second laser beam based on a power associated with the second laser beam;
a motorized stage configured to align the launcher unit to a base-line position based on the determined deviation of the second laser beam; and
a controller unit configured to identify a scattering of the second laser beam when the determined power loss is less than a determined threshold value and there is no deviation of the second laser beam from the determined position.

9. The auto-aligning spectroscopy system of claim 6, wherein the launcher unit is disposed adjacent to a first window of the chamber, and the receiver unit is disposed adjacent to a second window of the chamber, and wherein the second window is opposite to the first window.

10. The auto-aligning spectroscopy system of claim 6, wherein the controller unit is coupled to the motorized stage and the receiver unit and configured to:
generate an error signal based on the determined deviation of the second laser beam; and
drive the motorized stage based on the error signal to align the launcher unit to the base-line position.

11. The auto-aligning spectroscopy system of claim 6, wherein the second detector is configured to determine a direction of the deviation of the second laser beam from the determined position.

12. The auto-aligning spectroscopy system of claim 11, wherein the motorized stage is configured to orient the launcher unit based on the determined direction of the deviation of the second laser beam.

13. The auto-aligning spectroscopy system of claim 6, wherein the launcher unit comprises:
a first laser source configured to generate the first laser beam at a first wavelength, wherein the first laser beam is sensitive to one or more species in the chamber;
a second laser source configured to generate the second laser beam at a second wavelength, wherein the second laser beam is insensitive to the one or more species in the chamber;
a beam combiner configured to:
receive the first laser beam and the second laser beam;
combine the first laser beam with the second laser beam such that the first laser beam is co-linear with the second laser beam; and
a first lens disposed downstream of the beam combiner and configured to collimate the first laser beam with the second laser beam.

14. The auto-aligning spectroscopy system of claim 13, wherein the beam combiner comprises a first dichroic mirror disposed at a first determined angle and configured to:
transmit the first laser beam through the first dichroic mirror; and
reflect the second laser beam along a direction of the first laser beam.

15. The auto-aligning spectroscopy system of claim 8, wherein the receiver unit further comprises:
a second lens disposed adjacent to a second window of the chamber and configured to converge the first laser beam and the second laser beam; and
a beam splitter disposed adjacent to the second lens and configured to separate the first laser beam from the second laser beam.

16. The auto-aligning spectroscopy system of claim 15, wherein the beam splitter comprises a second dichroic mirror disposed at a second determined angle and configured to:
transmit the first laser beam through the second dichroic mirror such that the first laser beam is incident on the first detector; and
reflect the second laser beam such that the second laser beam is incident on the second detector.

* * * * *